Jan. 8, 1963 R. V. LINDQUIST Plant Pat. 2,214
ROSE PLANT
Filed March 27, 1962
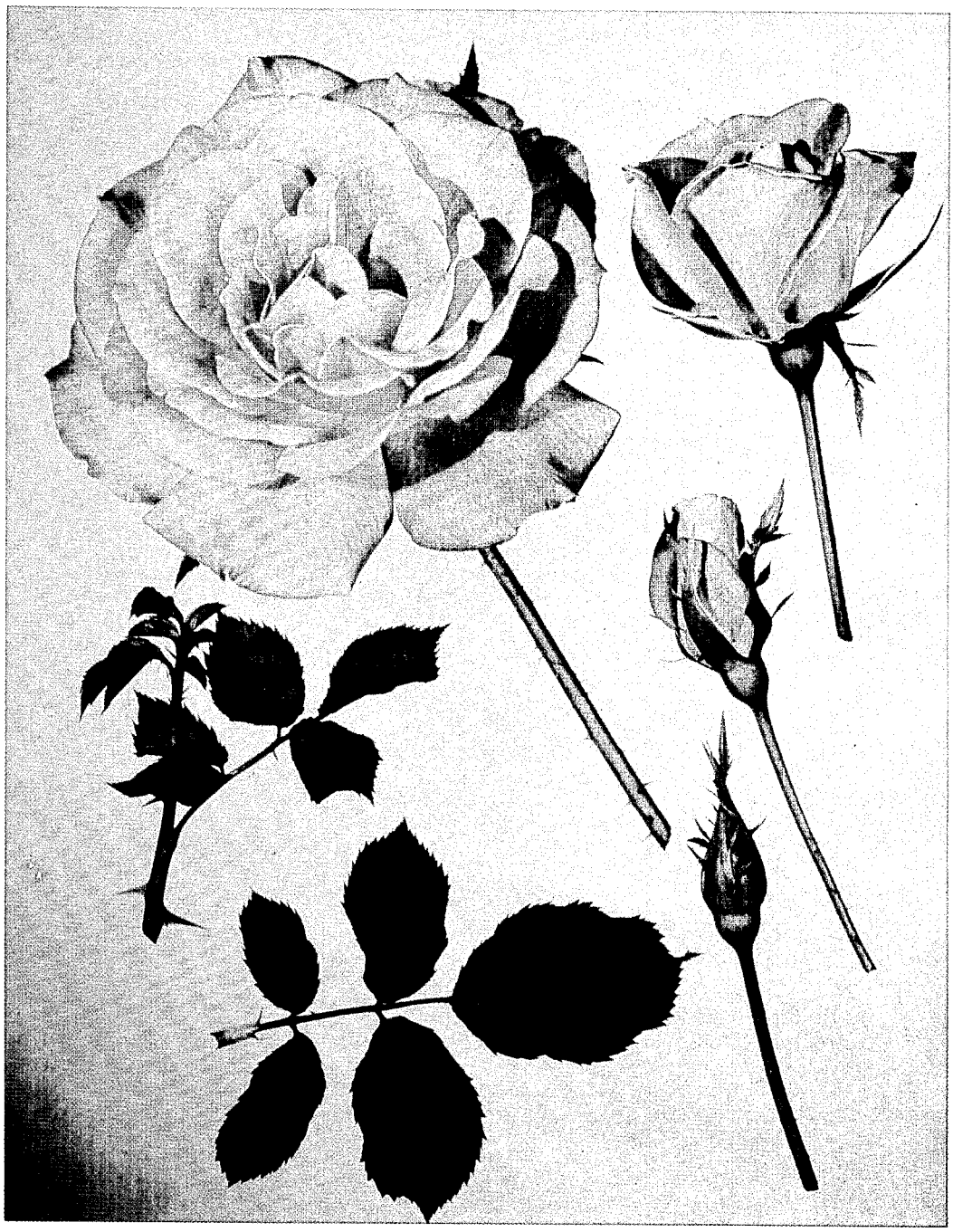
Inventor.
R. V. Lindquist
By: Robb & Robb
Attorneys.

United States Patent Office

Plant Pat. 2,214
Patented Jan. 8, 1963

2,214
ROSE PLANT

Robert V. Lindquist, Hemet, Calif., assignor to Hemet Wholesale, Hemet, Calif., a partnership Filed Mar. 27, 1962, Ser. No. 182,983
1 Claim. (Cl. 47—61)

The present invention relates to a new and distinct variety of rose plant of the hybrid tea class, which was originated by me by crossing the variety "Tiffany" (Plant Patent No. 1,304) with the variety "Cavalcade" (Plant Patent No. 991).

As the result of this breeding, I have produced a new rose variety which is particularly characterized as to novelty by the following unique combination of characteristics which are outstanding therein and which distinguish it from its parents, as well as from all other varieties of which I am aware:

(1) Distinctive foliage which is characterized by having wrinkled edges which give the foliage a holly-like appearance; and (2) A distinctive, attractive and unique blend of flower colors which create a multi-color effect different from any other rose known in commerce.

Asexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated:

Type: Hardy; bush; outdoor; seedling; for cut flowers and garden decoration.

Class: Hybrid tea.

Breeding: Seedling.

*Seed parent.*—"Tiffany."

*Pollen parent.*—"Cavalcade."

Propagation: Holds its distinguishing characteristics through succeeding propagations by budding.

*Flower*

Locality where grown and observed: Hemet, California.

Flowers borne: Usually singly, but sometimes 2 or more to stem; on stems of normal strength and of medium to long length.

Quantity of bloom: Free, both outdoors and in greenhouse.

Continuity: Continuous during growing season.

Fragrance: Moderate. Nature—tea.

Bud:

*Peduncle.*—Average length; average caliper; erect; almost smooth; few gland-tipped cilia; few prickles. Color—near Scheele's Green, Plate 860/1, page 175 (Wilson).

*Before calyx breaks.*—Size—medium. Form—Medium length; pointed; with foliaceous appendages and few gland-tipped cilia on the surface of the bud; usually with bristle-like foliaceous parts extending beyond the tip of the bud equal to ¼ or more of its length.

*As calyx breaks.*—Color—near Indian Lake, Plate 826, page 170 (Wilson).

*Sepals.*—Inner surface—with fine, wooly tomentum; some with foliaceous appendages lined with gland-tipped cilia and hairs.

*As first petal opens.*—Size—average. Form—medium length; urn-shaped. Color: outside—near Lemon Yellow, Plate 4/2, page 4 (Wilson), streaked and partly bordered with Rose Bengal, Plate 25/1, page 25 (Wilson), and with Lemon Yellow, Plate 4, page 4 (Wilson) at base; inside—near Rose Bengal, Plate 25, page 25 (Wilson) at outer edge, blending with shades of Nasturtium Red, Plate 14, page 14 (Wilson) and Scarlet, Plate 19, page 19 (Wilson) towards center of petal, and with Lemon Yellow, Plate 4, page 4 (Wilson) at base.

*Opening.*—Opens up well.

Bloom:

*Size (when fully open).*—From 4 inches to 5 inches.

*Petalage.*—Semi-double; from 18 to 25 petals, plus 4 to 6 petaloids; arranged irregularly.

*Form.*—High centered at first, but becoming somewhat flat to open; petals being at first rolled outward, but later becoming somewhat loosely rolled outward at maturity.

Petals:

*Texture.*—Medium thickness; moderately soft. Inside—slightly satiny. Outside—slightly satiny.

*Shape.*—Outside—round, with some petals having small point at apex. Intermediate—round, with some petals having small point at apex. Inside—nearly cuneate, with apex rounded and somewhat irregular.

This description of a newly opened flower was made from a rose grown in a greenhouse during the month of March at Hemet, California:

*Color.*—Outer petal: outside surface—near Lemon Yellow, plate 4/2, page 4 (Wilson), slightly veined and with patches of Rose Bengal, Plate 25/1, page 25 (Wilson), with Lemon Yellow, Plate 4, page 4 (Wilson) at base; inside surface—near Rose Bengal, Plate 25, page 25 (Wilson) at outer edge, blending with shades of Nasturtium Red, Plate 14/1, page 14 (Wilson) and Scarlet, Plate 19, page 19 (Wilson) towards center of petal, with Lemon Yellow, Plate 4, page 4 (Wilson) at base. Intermediate petal: outside surface—near Lemon Yellow, Plate 4/2, page 4 (Wilson), with slight shadings of Begonia, Plate 619/3, page 146 (Wilson) at extreme outer edge, with Lemon Yellow, Plate 4, page 4 (Wilson) at base; inside surface—near Begonia, Plate 619, page 146 (Wilson) at outer edge, with shades of near Nasturtium Red, Plate 14, page 14 (Wilson), and with Lemon Yellow, Plate 4, page 4 (Wilson) at base. Inner petal: outside surface—near Lemon Yellow, Plate 4/1, page 4 (Wilson), blending to Lemon Yellow, Plate 4, page 4 (Wilson) at base; inside surface—near Scarlet, Plate 19, page 19 (Wilson), with Lemon Yellow, Plate 4, page 4 (Wilson) at base.

This description was made from a rose that was open for three days in a greenhouse, during the month of March at Hemet, California:

*Color.*—Outer petal: outside surface—outer edge of petal near Rose Bengal, Plate 25/2, page 25 (Wilson), with main portion white and with increasing shades of Chinese Yellow, Plate 606/1, page 68 (Wilson) toward base, with near Chinese Yellow, Plate 606/2, page 68 (Wilson) at base; inside surface—near Rose Bengal, Plate 25/1, page 25 (Wilson) at outer edge, shading to near Rose Bengal, Plate 25/2, page 25 (Wilson), and with Lemon Yellow, Plate 4, page 4 (Wilson) at base. Inner petal: outside surface—near Lemon Yellow, Plate 4/3, page 4 (Wilson) at outer edge, with shadings of near Lemon Yellow, Plate 4/2, page 4 (Wilson), and with Lemon Yellow, Plate 4/1, page 4 (Wilson) at base; inside surface—near Orange Buff, Plate 507, page 133 (Wilson) near base, washing out to near Orange Buff, Plate 507/3, page 133 (Wilson) at outer edge, with some petals slightly bordered with Rose Bengal, Plate 25/2, page 25 (Wilson), and with Lemon Yellow, Plate 4, page 4 (Wilson) at base.

*General color effect.*—Newly opened flower—multi-color, with varying shades of Rose Bengal, Nasturtium Red and Lemon Yellow. 3-days open—multi-color, with varying shades of Rose Bengal, Nasturtium Red, and Lemon Yellow.

*Behavior.*—Drop off cleanly; when grown outdoors, bloom is reduced in petalage and size by hot, dry weather.

*Flower longevity.*—On bush in garden—from 3 to 5 days in May. Cut roses grown outdoors and kept at living-room temperatures—3 days in May. Cut roses grown in greenhouse and kept at living-room temperatures—3 or 4 days in March.

*Reproductive organs*

Stamens: Average number; arranged regularly about pistils.

Filaments: From short to medium length; most with anthers.

Anthers: Medium size; all open approximately at once. Color: upper side—near Yellow Ochre, Plate 07, page 101 (Wilson); under side—near Yellow Ochre, Plate 07/2, page 101 (Wilson).

Pollen: Somewhat moderate quantity. Color—near Yellow Ochre, Plate XV (Ridgway).

Pistils: Average number; approximately 75 in number.

Styles: Moderately uneven; from short to average length; average caliper; somewhat bunched.

Stigma: Color—near Apricot Yellow, Plate IV (Ridgway).

Ovaries: Most enclosed in calyx.

Hips: Short; globular; with inconspicuous neck; moderately smooth; walls thick and fleshy. Color—near Olive Ochre, Plate XXX (Ridgway) and sometimes near Dragon's Blood Red, Plate XIII (Ridgway).

Sepals: Falling soon; long; recurved. Color: inside—near Biscay Green, Plate XVII (Ridgway); outside—near Parrot Green, Plate VI (Ridgway).

Seeds: Few; from 8 to 17 in number; medium size.

*Plant*

Foliage:

*Leaves.*—Compound of usually 5 to 7 leaflets; medium size; somewhat leathery; wrinkled at edges, giving hollylike appearance.

*Leaflets.*—Shape—oval, with apex mucronate. Base—round. Margin—irregularly serrate.

*Color.*—Mature: upper surface—near Elm Green, Plate XVII (Ridgway); under surface—near Pois Green, Plate XLI (Ridgway), with some veins near Corinthian Purple, Plate XXXVIII (Ridgway). Young: upper surface—near Light Elm Green, Plate XVII (Ridgway); under surface—near Asphodel Green, Plate XLI (Ridgway), with some veins near Corinthian Purple, Plate XXXVIII (Ridgway).

*Rachis (the supporting stem of the compound leaf).*—Average size. Upper side—grooved; with some stipitate glands on edges. Under side—moderately smooth, but prickly, and with some thorns.

*Stipules.*—Medium length; narrow; with points of medium length turning out at an angle of more than 45°.

*Disease resistance.*—Mildly subject to mildew, as determined by comparison with other varieties grown under comparable cultural conditions at Hemet, California.

Growth:

*Habit.*—Bushy; upright; much-branched.

*Growth.*—Free; vigorous.

*Canes.*—Medium caliper.

*Main stems.*—Color—near Light Elm Green, Plate XVII (Ridgway). Large prickles—few; from medium length to long; curved slightly downward; with narrow base of medium length; color—near Sayal Brown, Plate XXIX (Ridgway). Small prickles—few; color—near Cinnamon Brown, Plate XXIX (Ridgway). Hairs—none.

*Branches.*—Color—near Biscay Green, Plate XVII (Ridgway). Large prickles—several; from medium length to long; curved slightly downward; with narrow base of medium length. Color—near Old Gold, Plate XVI (Ridgway). Small prickles—none. Hairs—none.

*New shoots.*—Color—near Oil Green, Plate V (Ridgway), veined with varying shades of Corinthian Purple, Plate XXXVIII (Ridgway). Large prickles—few; medium length; curved slightly downward; with narrow base of medium length; color—tip near Glass Green, Plate XXXI (Ridgway), with light shading of Corinthian Purple, Plate XXXVIII (Ridgway). Small prickles—none. Hairs—none.

I claim:

A new and distinct variety of rose plant of the hybrid tea class, substantially as herein shown and described, characterized particularly as to novelty by the unique combination of distinctive foliage having wrinkled edges which give the foliage a holly-like appearance, and a distinctive, attractive and unusual blend of flower colors which give the flowers a multi-color effect which is different from any other rose known in commerce.

No references cited.